United States Patent [19]
Arndt et al.

[11] Patent Number: 5,525,744
[45] Date of Patent: Jun. 11, 1996

[54] PROCESS FOR THE PREPARATION OF TETRACHLORO-1,4-BENZOQUINONE

[75] Inventors: Otto Arndt, Hofheim; Hans Schubert, Kelkheim, both of Germany

[73] Assignee: Hoechst Aktiengesellschaft, Germany

[21] Appl. No.: 327,033

[22] Filed: Oct. 21, 1994

[30] Foreign Application Priority Data

Oct. 25, 1993 [DE] Germany ............ 43 36 323.7

[51] Int. Cl.⁶ ............ C07C 50/24; C07C 46/00; C07C 46/06; C07C 46/10
[52] U.S. Cl. ............ 552/308
[58] Field of Search ............ 552/308

[56] References Cited

U.S. PATENT DOCUMENTS 5,149,850  9/1992  Arndt et al. .

FOREIGN PATENT DOCUMENTS 0220135  4/1987  European Pat. Off. .
0278378  1/1992  European Pat. Off. .

OTHER PUBLICATIONS

Derwent Publication Ltd. Class E 14, & JP-A-5 271 144, 1993.

Primary Examiner—Rebecca Cook
Attorney, Agent, or Firm—Connolly & Hutz

[57] ABSTRACT

A process for the preparation of tetrachloro-1,4-benzoquinone of high purity by the action of chlorine and concentrated hydrochloric acid on hydroquinone, by introducing a part of the hydroquinone to be employed into an initially introduced 4- to 6-fold molar amount—based on the total amount of hydroquinone—of 20 to 37 % aqueous hydrochloric acid containing catalytic amounts of iron(III) ions and an anionic dispersant, introducing 1.5 to 2.0 times the molar amount—based on total hydroquinone—of chlorine as a gas into this solution at a temperature of 20° to 90° C., then adding the residual amount of hydroquinone as a solid or in dissolved form, introducing 1.5 to 2.0 times the molar amount of chlorine as a gas, keeping the concentration of the hydrochloric acid here at 23–25% by addition of water and finally raising the temperature to 100° to 107° C. with further introduction of chlorine as a gas (1.7 to 2.5 times the molar amount) and dilution with water to a hydrochloric acid concentration of 20 to 22%.

16 Claims, No Drawings

PROCESS FOR THE PREPARATION OF TETRACHLORO-1,4-BENZOQUINONE

DESCRIPTION

Process for the preparation of tetrachloro- 1,4-benzoquinone

The invention relates to a process for the preparation of tetrachloro-1,4-benzoquinone of high purity by chlorination of hydroquinone.

Tetrachloro-1,4-benzoquinone (chloranil) is a useful intermediate for the preparation of dyestuffs and pesticides. It is also employed as a photographic chemical and vulcanizing agent and used as an additive for lubricants.

The preparation of chloranil from hydroquinone (1,4-dihydroxybenzene) or 1,4-benzoquinone or chlorinated 1,4-benzoquinone is known.

The EP Patent 0 220 135 describes e.g. a process in which hydrochloric acid and chlorine are initially introduced under pressure and chlorine and quinone, hydroquinone or their chlorine derivatives are metered in under pressure in separate streams.

EP Patent 0 278 378 describes a process in which the total amount of hydroquinone is initially introduced with hydrochloric acid and chlorine is then introduced as a gas at normal pressure according to a specific temperature and dilution program.

Both procedures have disadvantages:

The process according to EP 0 220 135 uses a chlorine pressure of 3 to 12 bar and requires an exact synchronized addition of the chlorine and hydroquinone streams.

The process according to EP 0 278 378 has the following disadvantages:

1.) As a result of the initial introduction of the total amount of hydroquinone, crusts are formed on the reactor wall in the course of the reaction. In addition, the reaction mixture goes through states of poor stirrability, as it becomes very thick during this process.
2.) The prolonged thermal loading of the reaction mixture at temperatures above 100° C. causes an impairment of quality due to traces of by-products.
3.) The long after-chlorination period causes a worsening of the space-time yield.

There is therefore a need for a process for the preparation of tetrachloro-1,4-benzoquinone, which is simple and technically easy to carry out, avoids the abovementioned disadvantages and makes tetrachloro-1,4-benzoquinone accessible not only in high purity, but also in high yield and space-time yield.

This object is achieved by a process for the preparation of tetrachloro-1,4-benzoquinone of high purity by the action of chlorine and concentrated hydrochloric acid on hydroquinone, which comprises introducing a part of the hydroquinone to be employed into an initially introduced 4- to 6-fold molar amount—based on the total amount of hydroquinone—of 20 to 37% aqueous hydrochloric acid containing catalytic amounts of iron(III) ions and an anionic dispersant, introducing 1.5 to 2.0 times the molar amount—based on total hydroquinone—of chlorine as a gas into this solution at a temperature of 20° to 90° C., then adding the residual amount of hydroquinone as a solid or in dissolved form, introducing 1.5 to 2.0 times the molar amount of chlorine as a gas, keeping the concentration of the hydrochloric acid here at 23–25% by addition of water and finally raising the temperature to 100° to 107° C. with further introduction of chlorine as a gas (1.7- to 2.5-fold molar amount) and dilution with water to a hydrochloric acid concentration of 20 to 22%.

In many cases it has proven suitable to employ 22 to 31% strength hydrochloric acid and to carry out the first phase of the chlorination at a temperature of 40° to 90° C., in particular 50° to 80° C. It has proven advantageous to initially introduce 30 to 70%, in particular 40 to 60%, preferably 45 to 55%, of the hydroquinone to be employed and to adjust the concentration of the hydrochloric acid to 22 to 28%, in particular 23 to 25%.

The chlorination proceeds advantageously in 5 to 15 hours, in particular 8.5 to 10.5 hours.

Surprisingly substantial improvements in space-time yield and product quality are achieved by this procedure in comparison to EP 0 278 378. The process modification is that the total amount of the hydroquinone is no longer initially introduced, but the hydroquinone is added to the mixture in two portions: the first part as an initial introduction together with the hydrochloric acid, the second part as a solid or in aqueous, approximately 10 to 20% strength, in particular 15–18% strength, solution at elevated temperature after the first introduction of chlorine as a gas. Water is added here in a constant stream such that the concentration of the hydrochloric acid is kept at about 23–25%. After completion of the first chlorination stage (formation of the polychlorinated quinhydrones) further chlorine is introduced as a gas, but now with an increase in temperature to close to the boiling point of the azeotropic hydrochloric acid (about 105° to 107° C.), whose concentration of about 20% is adjusted by addition of water. In this phase, the chlorine is also used to an increased extent for the oxidation of the chlorinated hydroquinones and quinhydrones, in addition to the introduction of the fourth Cl atom into the ring, the presence of traces of iron(III) ions as an oxidation catalyst having proven suitable.

If necessary, the quality of the isolated chloranil can be further improved by subsequent treatment with boiling water.

The advantages of this procedure in comparison with EP 0 278 378 are:

The technical feasibility of the reaction is improved: The stirrability is made easier despite decreased use of hydrochloric acid, the heat transfer is improved, the cooling brine is unnecessary, the homogeneity of the reaction mixture is produced by the absence of the crusts, the time consumption for the chlorination and oxidation is reduced (more rapid oxidation, better reaction of residual amounts of trichlorobenzoquinone), the amount of chlorine gas used and thus also the waste gas pollution by chlorine is decreased, and the quality of the product (evident from fewer components in the HPLC) and its reproducibility are improved.

The process is flexible in terms of temperature control and in the manner of addition of the second portion of hydroquinone.

The reasons for the improved process control and improved reproducibility in comparison to the cited prior art are:

a) working at normal pressure (safety aspects),
b) the simpler addition conditions (a temporary over-addition of chlorine is harmless with respect to waste gas pollution, since the chlorine is buffered by the hydroquinone, which is present in excess). The 2nd portion of hydroquinone can be added rapidly as a solid or as an aqueous solution before further introduction of chlorine as a gas or slowly with the further introduction of chlorine as a gas.
c) the simpler cooling technique (cooling at a higher temperature level), d) the better stirrability of the suspension despite decreased initial introduction of hydrochloric acid, e) the lower tendency for crust formation, f) the decrease in chlorine in the waste gas g) no hydrogen chloride in the waste gas, h) the more rapid oxidation of the intermediately formed polychlorinated quinhydrones and hydroquinones by the chlorine, i) the lower thermal load during the after-chlorination, j) the non-dependence on the composition of the gas atmosphere in the reactor (air or nitrogen), k) the constant quality, which avoids recrystallization, of the isolated chloranil.

The chloranil prepared according to the invention is of high purity (melting point, HPLC), and in comparison to the information in the cited EP 0 278 378 has less secondary components together with a simultaneously increased space-time yield.

The examples below are used to illustrate the process according to the invention without restricting it. Parts here are parts by weight.

EXAMPLE 1

First stage 27.65 parts of hydroquinone (0.25 mol) are introduced as a solid under an air atmosphere into 287 parts of 31% hydrochloric acid (2.4 mol) which contains 0.024 part of iron(III) chloride as an oxidation catalyst and 0.50 part of an anionic dispersant. 125 parts of chlorine (1.76 mol) are introduced as a gas at 55° C. in the course of 3 hours. 250 parts of warm water (55° C.) are simultaneously added. When 50% of the chlorine and the water has been added, 27.65 parts of hydroquinone (0.25 mol) are added as a solid in a single portion. The reaction, progressing through all chlorination stages according to HPLC, is already now accompanied by the oxidation leading to the chlorinated benzoquinone (oxidant=chlorine). A readily stirrable, crust-free, yellow-brown suspension is obtained. The waste gas is monitored. No chlorine and no hydrogen chloride must pass into the waste gas. The concentration of the hydrochloric acid is about 25%.

Second stage

The mixture of polychlorinated benzoquinones and hydroquinones (or quinhydrones) is heated to 85° C. in the course of 3 hours with further introduction of 50 parts of chlorine as a gas (=0.70 mol). After 50% of the chlorine has been introduced as a gas, 250 parts of water are added. The concentration of the hydrochloric acid before dilution is about 27%, afterwards about 20%. The oxidation is completed in the second stage. A readily stirrable, crust-free, yellow suspension of tetrachlorobenzoquinone is obtained, which still contains some trichlorobenzoquinone. The waste gas is monitored. Only a little chlorine (at most 7 parts=0.1 mol) must pass into the waste gas.

Third stage

The suspension is heated to 105° C. in the course of about 1 hour. In this stage, still no hydrogen chloride must escape.

Fourth stage

The temperature of the reaction mixture is kept at 103° to 106° C., preferably 105° C., for 3 hours. During the course of this, chlorine is introduced again as a gas (at most 25 parts=0.35 mol). The oxidation of residual tetrachlorohydroquinone and the completion of the chlorination of residual trichlorobenzoquinone to tetrachlorobenzoquinone (=chloranil) are monitored by TLC and HPLC. The waste gas now contains about 7 parts of chlorine (=about 0.1 mol). The reaction is carried out in all stages in an open system (ventilation via waste gas unit) so that no pressure can build up. The chlorination time is at most 10 hours. Altogether, 200 parts of chlorine (2.82 mol) are introduced as a gas. The mixture is cooled to 40° C. while blanketing with protective gas (nitrogen), by means of which sucking back of chlorine from the waste gas absorption is prevented and the atmosphere over the reaction mixture is detoxified. After filtration at 40° C. and washing with 500 parts of water, 119 parts of yellow chloranil having a purity of 98% are obtained (0.474 mol), corresponding to a yield of 95%. Tetrachlorohydroquinone or other polychlorinated quinhydrones and hydroquinones are not detectable (TLC). The content of 2,3,5-trichlorobenzoquinone is at most 2.0% by weight (HPLC).

The mother liquor (795 parts) is an approximately 21% strength hydrochloric acid (4.6 mol of HCl), and the wash filtrate (503 parts) contains about 4.4%=0.6 mol of HCl. The chlorine balance (hydrogen chloride and chlorine, including waste gas) is about 95% of theory. The reacted chlorine corresponds to theory. At the start of the fourth stage small amounts of tetrachlorohydroquinone are still present (TLC).

EXAMPLE 2

First stage

The procedure is as in Example 1, but at a temperature of 70° C. and using only 125 parts of water. The addition of the second portion of hydroquinone is carried out as an approximately 18% strength aqueous solution at 70° C. (containing 125 parts of water) either rapidly before the second portion of chlorine or simultaneously with the second portion of chlorine. No waste gas is produced in this stage.

Second stage 45 parts of chlorine (0.63 mol) are introduced as a gas at 70° C. (retention of the temperature of the first stage) in the course of 2 hours. 200 parts of water are then added. The concentration of the hydrochloric acid before dilution is about 28%, afterwards about 21%. The oxidation is completed in the second stage.

Third stage

The mixture is heated to 105° C. in the course of 3 hours with further introduction of 25 parts of chlorine as a gas (0.35 mol). The addition of HCl to trichlorobenzoquinone is avoided. The waste gas from the 2nd and 3rd stages contains 23 parts of chlorine.

Fourth stage

The temperature is kept at 103° to 106° C., preferably 105° C., for 2 hours. During the course of this, at most 15 parts (0.21 mol) of chlorine are introduced as a gas. The waste gas contains 10 parts of chlorine. The total chlorination time (over all stages) is 10 hours. Altogether 210 parts of chlorine are introduced as a gas. 120 parts of chloranil having a purity of 98.3% are obtained (0.480 mol), corresponding to a yield of 96%. Tetrachlorohydroquinone or other polychlorinated quinhydrones and hydroquinones are not detectable (TLC). The content of 2,3,5-trichlorobenzoquinone is at most 1.7% by weight (HPLC), the content of pentachlorophenol about 100 µg/g. The chlorine balance (hydrogen chloride and chlorine, including waste gas) is about 100% of theory. The chlorine conversion is 99.4% of theory. At the start of the third stage polychlorinated hydroquinone or quinhydrone is no longer present.

EXAMPLE 3

(Subsequent treatment with water)

30 parts of a chloranil sample having a melting point of 270° to 274° C., a content of polychlorinated quinhydrones and hydroquinones still detectable in traces by thin-layer chromatography and a content of pentachlorophenol of 120 µg/g are treated in 125 parts of water at 100° C. for 2 hours and then filtered at 90° C. 29 parts of chloranil having a melting point of 293° to 295° C., a content of polychlorinatedquinhydrones and hydroquinones which is no longer detectable by thin-layer chromatography and a content of pentachlorophenol of less than 20 µg/g are obtained.

We claim:

1. A process for the preparation of tetrachloro-1,4-benzoquinone from hydroquinone in the presence of an aqueous medium containing chlorine and hydrochloric acid, which comprises the steps of:

providing an aqueous medium containing iron (III) ions as a catalyst, an anionic dispersant, and hydrochloric acid in a concentration of 20 to 37%, said hydrochloric acid being provided in a 4 to 6 times molar amount based on the total amount of hydroquinone to be added in said process;

dividing said total amount of hydroquinone into space-time yield-improving portions and introducing a first portion of the hydroquinone into said aqueous medium;

introducing 1.5 to 2.0 times the molar amount, based on said total amount hydroquinone, of chlorine as a gas into the aqueous medium at a temperature of from 20° to 90° C. in a first chlorine addition;

adding the remaining portion of hydroquinone;

introducing 1.5 to 2.0 times the molar amount, based on said total amount of hydroquinone, of chlorine as a gas in a second chlorine addition;

holding the concentration of the hydrochloric acid in the aqueous medium at 23–25% by addition of water;

raising the temperature to 100° to 107° C. while introducing additional chlorine gas at 1.7 to 2.5 times the total molar amount of hydroquinone in a third chlorine addition; and diluting the aqueous medium with water to a hydrochloric acid concentration of from 20 to 22%.

2. The process as claimed in claim 1, wherein 30 to 70% of the total amount of hydroquinone to be added in said process is introduced as a said first portion thereof.

3. The process as claimed in claim 2, wherein said first portion of hydroquinone is 40 to 60% of said total amount.

4. The process as claimed in claim 1, wherein said first portion of hydroquinone is 45 to 55% of said total amount.

5. The process as claimed in claim 1, wherein, in said providing step, the concentration of hydrochloric acid in said aqueous medium is 22 to 28%.

6. The process as claimed in claim 1, wherein, in said providing step, the concentration of hydrochloric acid in said aqueous medium is 23 to 25%.

7. The process as claimed in claim 1, wherein, in said first chlorine addition, said temperature is from 40° to 90° C.

8. The process as claimed in claim 7, wherein said temperature is from 50° to 80° C.

9. The process as claimed in claim 1, wherein the remaining portion of hydroquinone is added as an aqueous solution having a hydroquinone concentration of 10 to 20%.

10. The process as claimed in claim 9, wherein said hydroquinone concentration is 15 to 18%.

11. The process as claimed in claim 1, wherein, in said third chlorine addition, said temperature is from 103° to 106° C.

12. The process as claimed in claim 11, wherein said temperature is from 104° to 105° C.

13. The process as claimed in claim 1, wherein all three chlorine additions are carried out in the course of 5 to 15 hours.

14. The process as claimed in claim 1, wherein all three chlorine additions are carried out in the course of 5 to 10.5 hours.

15. The process as claimed in claim 1, wherein tetrachloro1,4-benzoquinone is isolated.

16. The process as claimed in claim 15, wherein the thus-isolated tetrachloro-1,4-benzoquinone is treated with boiling water.

* * * * *